United States Patent [19]

Saunders

[11] 4,300,245
[45] Nov. 17, 1981

[54] PNEUMATIC LEG

[75] Inventor: Gerald A. Saunders, Bath, Canada

[73] Assignee: Queen's University at Kingston, Kingston, Canada

[21] Appl. No.: 181,153

[22] Filed: Aug. 25, 1980

Related U.S. Application Data

[63] Continuation-in-part of Ser. No. 101,597, Dec. 10, 1979, abandoned.

[51] Int. Cl.$^3$ .............................................. A61F 1/12
[52] U.S. Cl. .............................................. 3/18; 3/20; 128/DIG. 20
[58] Field of Search .................... 3/2, 17 R, 17 SS, 19, 3/20, 18; 128/DIG. 20

[56] References Cited

U.S. PATENT DOCUMENTS

| | | | |
|---|---|---|---|
| 1,525,633 | 2/1925 | Witmyer | 3/17 R |
| 2,634,424 | 4/1953 | O'Gorman | 3/20 |
| 3,561,435 | 2/1971 | Nicholson | 128/DIG. 20 |
| 4,161,042 | 7/1979 | Cottingham et al. | 3/21 X |

FOREIGN PATENT DOCUMENTS

| | | | |
|---|---|---|---|
| 263203 | 7/1968 | Austria | 128/DIG. 20 |
| 470174 | 5/1969 | Switzerland | 128/DIG. 20 |
| 1171361 | 11/1969 | United Kingdom | 128/DIG. 20 |

Primary Examiner—Clifford D. Crowder
Attorney, Agent, or Firm—Stanley E. Johnson; Richard J. Hicks

[57] ABSTRACT

An artificial limb consisting of a tube like member having an inner wall and an outer wall, each of flexible air impervious material sealingly joined together at respectively opposite ends of the tube and along at least three lines extending longitudinally of the tube. The longitudinal seams are spaced apart from one another providing a plurality of side by side air inflatable compartments. At least one compartment is provided with an air inlet passage means for inflating the artificial limb and the compartments are in communication with one another so that there is equalization of pressure in all of the chambers. The inner and outer walls are preferably a transparent plastics material and the tube tapers in a direction from one end to the other. A protective cap may be detachably mounted on the lower end of the limb and such cap may be provided with fins projecting into the sleeve to stiffen the same if so desired.

9 Claims, 7 Drawing Figures

U.S. Patent   Nov. 17, 1981   4,300,245
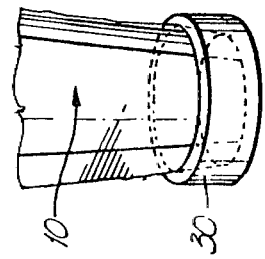
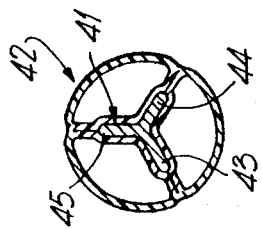
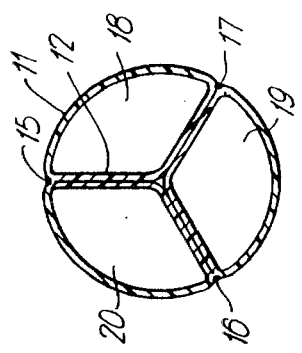
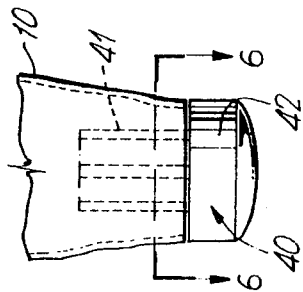
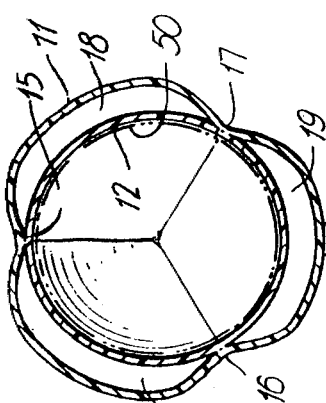
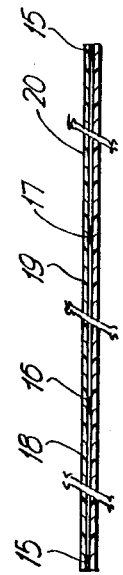
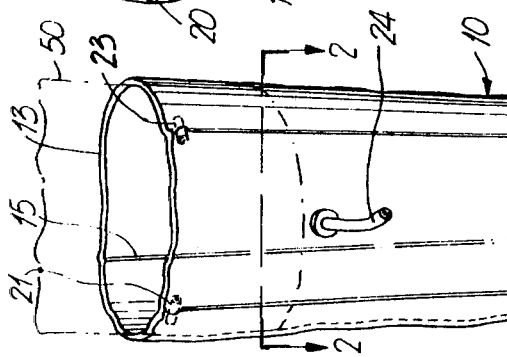

PNEUMATIC LEG

This is a continuation-in-part of application Ser. No. 101,597 filed Dec. 10, 1979, now abandoned.

This invention relates generally to artificial limbs and more particularly to an inflatable artificial leg.

Artificial limbs are known which have an air sac as a component part thereof and effectively the air sac serves as a cushion type connection between the leg stump and the rigid structure of the prosthetic device. Examples of prior art devices incorporating an air sac are disclosed in Canadian Pat. No. 1,027,303 issued Mar. 7, 1978
Canadian Pat. No. 63,398 issued Sept. 9, 1898
and
Canadian Pat. No. 507,275 issued Nov. 9, 1954.

The air sacs of such devices are not used by themselves nor would they be suitable for such use.

A principal object of the present invention is to provide an inflatable artificial leg that is used by itself without any rigidifying structure. The inflatable artificial leg of the present invention is primarily intended for use immediately after the amputation of a limb and after extended use of a conventional prothesis (artificial leg). By making the inflatable artificial limb from a transparent material, examination of the stump after surgery can be made without removing the artificial limb. The present practice after surgery involves applying a plaster cast or pressure bandages to control swelling. Plaster casts, however, are awkward, heavy and preclude examination of the stump. Pressure bandages are also awkward to apply, tighten and remove. The inflatable, artificial leg of the present invention can be used immediately after surgery, it permits examination of the stump without having to be removed and is constructed in such a manner that, without further supporting structure, it may be utilized by itself to support at least a part of the patient's weight.

In accordance with the present invention there is provided an inflatable artificial leg comprising a tube like member having an inner wall and an outer wall of flexible air impervious material and wherein the inner and outer walls are sealingly joined together longitudinally along the tube along at least three lines spaced apart from one another circumferentially around the tube providing a plurality of side-by-side air inflatable compartments that extend longitudinally along the length of the tube. Air passage means from one compartment to an adjacent compartment provides intercommunication of the compartments to equalize pressure in the same. An air passage inlet means into one of the compartments permits inflating the same. The tube is open at one end for insertion of the stump of a limb thereinto and the tube preferably tapers therefrom in a direction toward the other end. When in the inflated state, the inner wall of the compartments are in contact with one another thus providing at least three interengaged inflated compartments that have sufficient rigidity to support at least a portion of the user's weight without the need of any other supporting structure on the artificial limb.

The invention is illustrated by way of example in the accompanying drawings, wherein:

FIG. 1 is an oblique view of an artificial leg provided in accordance with the present invention and in an inflated state;

FIG. 2 is a cross-section taken along section 2—2 of FIG. 1;

FIG. 3 is a cross-sectional view taken along line 3—3 of FIG. 1;

FIG. 4 is a partial view of the lower end of the artificial leg having a protective cap thereon;

FIG. 5 is a partial view similar to FIG. 4 illustrating a modified protective lower end for the artificial limb;

FIG. 6 is a cross-sectional view taken along line 6—6 of FIG. 5; and

FIG. 7 is a cross-sectional view showing the inner and outer walls joined together before having the marginal edges thereof joined to form a tube.

Referring now to the drawings, there is illustrated an inflatable artificial leg 10 in the form of a longitudinally extending tubular like member having an outer wall 11 and an inner wall 12 each of a flexible air impervious material. The material is preferably a heat sealable thermoplastics material, i.e. polyvinylchloride, although other flexible sealable air impervious materials such as rubber may be used. The outer wall is preferably of a thicker material than the inner wall. The outer wall, for example, may be 0.016" thick to provide a rigid, tough and puncture resistant surface, and the inner wall much thinner, for example, 0.008" thick which allows it to readily mould around the contour of the stump. The inner and outer walls 11 and 12 are welded together at the respective opposite ends 13 and 14 and along three lines or seams 15, 16 & 17 that extend longitudinally of the tube from one end to the other. The longitudinal welds 15, 16 and 17 are equally spaced from one another circumferentially around the tube and taper inwardly slightly from the stump end 13 of the artificial limb to the foot end 14. The longitudinal welds 15, 16 and 17 provide three inflatable compartments 18, 19 and 20 interconnected for communication with one another by tubes 21 and 23 or other suitable air passage means. This intercommunication of the chambers equalizes pressurization of the three chambers, ensuring a stiffness in all directions throughout the length of the leg and equalization of pressure of the tube around the stump. The equalization of pressure from one chamber to the other also causes self-centering of the stump in the inflated artificial limb.

As illustrated in FIGS. 1 and 2, the stump 50 is inserted into the top end of the tube and there is an equal distribution of pressure around the stump by the inner wall 12. The tapered longitudinal walls provide effectively a three jaw clamping of the stump and as previously mentioned the stump is centrally clamped ensuring equal pressure distribution. The three jaw clamping and the tapering causes a tight grip on the stump, resisting being pulled off and thus overcoming a serious problem with short stumps. The leg is very light, its length can be easily adjusted and is reusable, one size fitting a wide range of patients. It is extremely cheap to manufacture and can be provided in various different lengths for different purposes and locations. Below the stump, the inner walls of the respective inflatable chambers 18, 19 and 20 inter-engage one another and thus provide a relatively stiff structure from below the stump to the foot end 14 of the artificial leg.

The bottom end of the artificial leg may be protected by a cap member 30 as illustrated in FIG. 4 or a combined cap and stem member 40 as illustrated in FIG. 5. The cap and stem member 40, illustrated in FIG. 5, has a stem 41 insertable into the lower end of the inflatable artificial leg and a ground engaging cap portion 42. The insertable stem 41 has three fins 43, 44 and 45 directed radially outwardly from the center of the member 40 which fit in between the air chambers 18, 19 and 20. The arrangement of FIG. 5 advantageously supports or stiffens the weakest portion of the inflated artificial leg and which is the lowermost portion. Obviously, the length of the stem 41 may be such as to rigidify the inflated artificial leg to the extent it supports the users weight. The artificial leg is effectively a slender tube-like column and the slenderness ratio thereof can be modified by or determined by the length of the fins.

In FIG. 7 there is illustrated diagrammatically a method of making the tube which consists of lying the two layers of plastic 11 and 12, one on top of the other, and welding the same together along the outer marginal edges by seams 15 and intermediate therebetween by seams 16 and 17. The ends are similarly welded together (see 13 and 14 in FIG. 1) whereafter the marginal edge seams 15 are brought into overlapping relationship and welded together. The welding is preferably by high frequency or dielectric sealing although other means of welding or sealing, well known in the art, may be used.

I claim:

1. An artificial limb comprising a tube like member having an inner wall and an outer wall, each of flexible air impervious material, sealingly joined together at respectively opposite ends of the tube and along at least three lines longitudinally of the tube, said longitudinal lines being spaced apart from one another circumferentially around the tube providing a plurality of side-by-side air inflatable compartments extending longitudinally along the length of the tube, means providing intercommunication of the compartments to equalize pressure in the same, and air passage inlet means into one of the compartments for use in inflating the same, said tube like member being open at one end for insertion of the stump of a limb thereinto and tapering therefrom toward the other end, said compartments when inflated providing a multi-jaw clamping of a stump inserted into one end of said tube and beyond which stump the inner wall of the respective compartments interengage one another stiffening the artificial limb.

2. An artificial limb as defined in claim 1 wherein said inner and outer walls are a heat sealable thermoplastics material.

3. An artificial limb as defined in claim 2 wherein said thermoplastics material is polyvinylchloride.

4. An artificial limb as defined in claim 1 wherein the thickness of material of the outer wall is greater than the thickness of the inner wall.

5. An artificial limb as defined in claim 1 wherein said inner and outer walls are each transparent sheets of polyvinylchloride and wherein the outer wall has a thickness of approximately 0.016" and the inner wall has a thickness of approximately 0.008".

6. An artificial limb as defined in claim 1 including one-way valve means in said air passage inlet means for retaining the compartments in a pressurized state.

7. An artificial limb as defined in claim 1 including a protective cap detachably mounted on an end thereof opposite said one end.

8. An artificial limb comprising a tube like member having an inner wall and an outer wall, each of flexible air impervious material, sealingly joined together at respectively opposite ends of the tube and along at least three lines longitudinally of the tube, said longitudinal lines being spaced apart from one another circumferentially around the tube providing a plurality of side-by-side air inflatable compartments extending longitudinally along the length of the tube, means providing intercommunication of the compartments to equalize pressure in the same, air passage inlet means into one of the compartments for use in inflating the same, said tube like member being open at one end for insertion of the stump of a limb thereinto and tapering therefrom toward the other end, said compartments when inflated providing a multi-jaw clamping of a stump inserted into one end of said tube and beyond which stump the inner wall of the respective compartments interengage one another stiffening the artificial limb, and including a protective cap detachably mounted on an end of the tube opposite said one end, said cap having a stem thereon projecting into said tube between said air inflatable compartments.

9. An artificial limb as defined in claim 8 wherein said stem has fins clampingly engaged between the inner walls of adjacently disposed compartments when the latter are inflated.

* * * * *